United States Patent [19]

Hindley et al.

[11] Patent Number: 5,075,300

[45] Date of Patent: Dec. 24, 1991

[54] NOVEL COMPOUNDS

[75] Inventors: Richard M. Hindley; David Haigh; Peter T. Duff, all of Epsom, England

[73] Assignee: Beecham Group p.l.c., Brentford, England

[21] Appl. No.: 398,490

[22] Filed: Aug. 25, 1989

[30] Foreign Application Priority Data

Aug. 26, 1988 [GB] United Kingdom ............... 8820389

[51] Int. Cl.$^5$ ............... C07D 417/12; A61K 31/425; A61K 31/44; A61K 31/505
[52] U.S. Cl. ............................ 514/269; 514/342; 514/369; 544/284; 544/316; 546/157; 546/280; 548/170; 548/181; 548/183
[58] Field of Search ............... 548/183, 181, 170; 514/369, 342, 269; 546/280, 157; 544/316, 284

[56] References Cited

FOREIGN PATENT DOCUMENTS 0008203 2/1980 European Pat. Off. ............ 514/367
0193256 9/1986 European Pat. Off. ............ 514/367
0306228 3/1989 European Pat. Off. ............ 514/367

OTHER PUBLICATIONS

Chemical and Pharmaceutical Bulletin, vol. 30, No. 10, pp. 3580–3600 (1982); T. Sohda et al., "Studies on Antidiabetic Agents".

Primary Examiner—Robert Gerstl
Attorney, Agent, or Firm—Hopgood, Calimafde, Kalil, Blaustein & Judlowe

[57] ABSTRACT

A compound of formula (I):

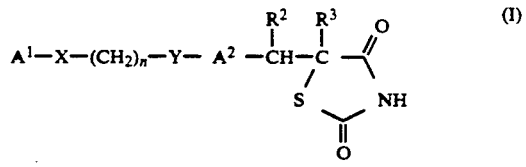

or a tautomeric form thereof and/or a pharamaceutically acceptable salt thereof, and/or a pharmaceutically acceptable solvate thereof, wherein:

$A^1$ represents a substituted or unsubstituted aromatic heterocyclyl group;

$A^2$ represents a benzene ring having in total up to five substituents;

X represents O, S or $NR^{1 \text{ } l \text{ wherein } R^1}$ represents a hydrogen atom, an alkyl group, an acyl group, an aralkyl group, wherein the aryl moiety may be substituted or unsubstituted, or a substituted or unsubstituted aryl group;

Y represents O or S providing that Y does not represent O when X represents $NR^1$;

$R^2$ and $R^3$ each represent hydrogen, or $R^2$ and $R^3$ together represent a bond; and n represents an integer in the range of from 2 to 6; a process for preparing such a compound; a pharmaceutical composition comprising such a compound; and the use of such a compound and a composition in medicine.

15 Claims, No Drawings

NOVEL COMPOUNDS

This invention relates to certain substituted thiazolidinedione derivatives, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581 and 0208420 relate to thiazolidinedione derivatives which are disclosed as having hypoglycaemic and hypolipidaemic activity. Chem. Pharm. Bull 30 (10) 3580–3600 also relates to certain thiazolidinedione derivatives having hypoglycaemic and hypolipidaemic activities.

It has now surprisingly been discovered that certain novel substituted-thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

$$A^1-X-(CH_2)_n-Y-A^2-CH-C \begin{array}{c} R^2 \; R^3 \\ | \; | \end{array} \begin{array}{c} O \\ \diagup \\ \diagdown \end{array} NH \quad (I)$$

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$A^2$ represents a benzene ring having in total up to five substituents;

X represents O, S or $NR^1$ wherein $R^1$ represents a hydrogen atom, an alkyl group, an acyl group, an aralkyl group, wherein the aryl moiety may be substituted or unsubstituted, or a substituted or unsubstituted aryl group;

Y represents O or S providing that Y does not represent O when X represents $NR^1$;

$R^2$ and $R^3$ each represent hydrogen, or $R^2$ and $R^3$ together represent a bond; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 or 2, selected from oxygen, sulphur or nitrogen.

Suitable values for $A^1$ when it represents a 5- membered aromatic heterocyclyl group include thiazolyl and oxazolyl, especially oxazolyl.

Suitable values for $A^1$ when it represents a 6- membered aromatic heterocyclyl group include pyridyl or pyrimidinyl.

Suitably $R^2$ and $R^3$ each represent hydrogen.

Preferably, $A^1$ represents a moiety of formula (a), (b) or (c):

wherein:

$R^4$ and $R^5$ each independently represents a hydrogen atom, an alkyl group or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of formula (a)

$X^1$ represents oxygen or sulphur.

Aptly, $A^1$ represents a moiety of the abovedefined formula (a).

Aptly, $A^1$ represents a moiety of the abovedefined formula (b).

Aptly, $A^1$ represents a moiety of the abovedefined formula (c).

In one favoured aspect $R^4$ and $R^5$ together represent a moiety of formula (d):

wherein $R^6$ and $R^7$ each independently represent hydrogen, halogen, substituted or unsubstituted alkyl or alkoxy.

Suitably, $R^6$ and $R^7$ each independently represent hydrogen, halogen, alkyl or alkoxy. Favourably, $R^6$ represents hydrogen. Favourably, $R^7$ represents hydrogen. Preferably, $R^6$ and $R^7$ both represent hydrogen.

In a further favoured aspect $R^4$ and $R^5$ each independently represent hydrogen, alkyl or a substituted or unsubstituted phenyl group and more favourably, $R^4$ and $R^5$ each independently represent hydrogen, alkyl or phenyl.

Preferably, for the moiety of formula (a), $R^4$ and $R^5$ together represent the moiety of formula (d).

Preferably, for the moieties of formula (b) or (c), $R^4$ and $R^5$ both represent hydrogen.

As stated in relation to formula (I), $A^2$ may have in total up to five substituents and thus $A^2$ may have up to three optional substituents which optional substituents are favourably selected from halogen, substituted or unsubstituted alkyl or alkoxy.

Favourably, $A^2$ represents a moiety of formula (e):

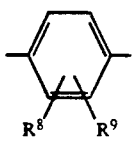

wherein R[8] and R[9] each independently represent hydrogen, halogen, substituted or unsubstituted alkyl or alkoxy.

Suitably, R[8] and R[9] each independently represent hydrogen, halogen, alkyl or alkoxy. Preferably, R[8] and R[9] each represent hydrogen. Favourably, X represents O. Favourably, X represents S.

Favourably, Y represents O. Favourably Y represents S.

Preferably, X and Y both represent O.

In one preferred aspect the present invention provides a class of compounds, which fall wholly within the scope of formula (I), of formula (II):

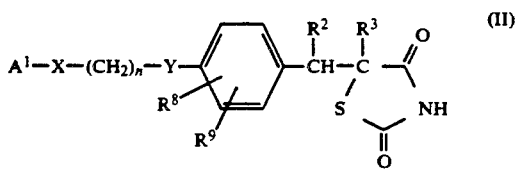

or a tautomeric form thereof, and/or a pharmaceutically acceptable salt thereof and/or a pharmaceutically acceptable solvate thereof, wherein $A^1$, X, Y, $R^2$, $R^3$, and n are as defined in relation to formula (I) and R[8] and R[9] are as defined in relation to formula (e).

Suitably, n represents an integer 2, 3 or 4, notably 2 or 3 and especially 2.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a phenylene group, and wherein the carbon atoms of the aryl group represented by the said two substituents may themselves be substituted or unsubstituted.

When used herein, unless otherwise stated, the term 'aryl' includes phenyl and naphthyl; any aryl group mentioned herein may be optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the terms 'alkyl' and 'alkoxy' relate to groups having straight or branched carbon chains, containing up to 12 carbon atoms. Thus, suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term "aryl".

Suitable pharmaceutically acceptable salts include salts of the thiazolidinedione moiety, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (III):

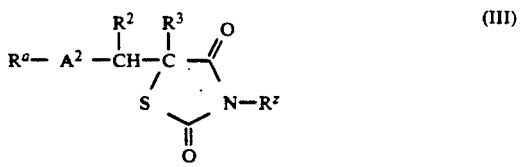

wherein $R^2$, $R^3$ and $A^2$ are as defined in relation to formula (I), $R^z$ is hydrogen or a nitrogen protecting group and $R^a$ is a moiety convertible to a moiety of formula (f):

wherein $A^1$, X, Y and n are as defined in relation to formula (I), with an appropriate reagent capable of converting $R^a$ to the said moiety (f) and thereafter, if required, carrying out one or more of the following optional steps:

(i) converting a compound of formula (I) to a further compound of formula (I); (ii) removing any protecting group;

(iii) preparing a pharmaceutically acceptable salt of the compound of formula (I) and/or a pharmaceutically acceptable solvate thereof.

Suitably, $R^a$ represents HX—$(CH_2)_n$—Y—wherein X, Y and n are as defined in relation to formula (I) although Y is preferably —O—.

When $R^a$ is HX—$(CH_2)_n$—Y—, an appropriate reagent capable of converting $R^a$ to a moiety (f) is a compound of formula (IV):

wherein A¹ is as defined in relation to formula (I) and R$^x$ represents a leaving group.

A suitable leaving group R$^x$ includes a halogen atom, preferably a chlorine or bromine atom, or a thioalkyl group for example a thiomethyl group.

Suitable values of HX—(CH$_2$)$_n$—Y—include HO(CH$_2$)$_n$—O—.

The reaction between the compound of formula (III) and the appropriate reagent may be carried out under conditions suitable to the particular compound of formula (III) and the reagent chosen; thus for example the abovementioned reaction between a compound of formula (III) wherein R$^a$ represents HX—(CH$_2$)$_n$—Y—and the compound of formula (IV), may be carried out in any suitable solvent, for example dimethylformamide, at a temperature which provides a suitable rate of formation of the compound of formula (I), for example at an elevated temperature in the range of from 50° C. to 120° C., preferably in the presence of a base such as sodium hydride.

A compound of formula (III) may be prepared from a compound of formula (V):

wherein A² is as defined in relation to the compound of formula (I) and R$^b$ is a moiety R$^a$, or a moiety convertible to a moiety R$^a$; by reaction of the compound of formula (V) with 2,4-thiazolidinedione; and thereafter if required carrying out one or more of the following optional steps:

(i) reducing a compound of formula (III) wherein R² and R³ together represent a bond, into a compound of formula (III) wherein R² and R³ each represent hydrogen;

(ii) converting a moiety R$^b$ to a moiety R$^a$.

The reaction between the compound of formula (V) and 2,4-thiazolidinedione will of course be carried out under conditions suitable to the nature of the compound of formula (V), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (V) and 2,4-thiazolidinedione, the water produced in the reaction is removed from the reaction mixture, for example by means of a Dean and Stark apparatus.

When R$^a$ represents HX—(CH$_2$)$_n$—Y—, a suitable value for R$^b$ is —YH.

When R$^a$ represents HX—(CH$_2$)$_n$—O—, a suitable value for R$^b$ is —OH.

When R$_a$ represents HX—(CH$_2$)$_n$—S—, a suitable value for R$^b$ is —SH.

The moiety R$^b$ may be converted to the moiety R$^a$ by any suitable means, for example when R$^b$ represents —OH or —SH and R$^a$ represents HX—(CH$_2$)$_n$—O—or HX—(CH$_2$)$_n$—S—the appropriate conversion may be carried out by coupling a compound of formula (VA):

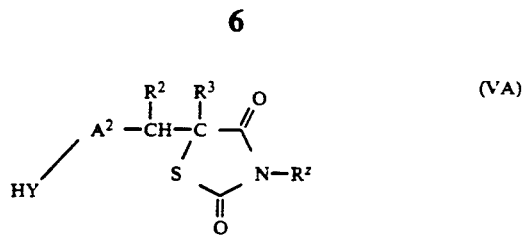

wherein R², R³, Y and A² are as defined in relation to formula (I) and R$^z$ is hydrogen or a nitrogen protecting group, with a compound of formula (VI):

wherein X and n are as defined in relation to formula (I), R$^y$ is a protecting group and, when Y in the compound of formula (VA) represents —O—, R$^x$ is hydrogen or, when Y in compound (VA) represents —S—, then R$^x$ is a tosylate or mesylate group; and thereafter, if required, carrying out one or more of the following optional steps:

(i) reducing a compound of formula (III) wherein R² and R³ together represent a bond, to a compound of formula (III) wherein R² and R³ each represent hydrogen;

(ii) removing any protecting group.

When Y in (VA) is —O—and R$^x$ in (VI) is hydrogen, the reaction is generally carried out in the presence of a suitable coupling agent; a suitable coupling agent being diethylazodicarboxylate and triphenylphosphine. The coupling reaction may be carried out in any suitable solvent at a low to medium temperature, for example in tetrahydrofuran at a temperature in the range of between 0° and 60° C.

When Y in (VA) is —S—and R$^x$ in (VI) represents tosylate or mesylate, the reaction between (VA) and (VI) is suitably carried out in an aprotic solvent, such as dimethylformamide, at a low to elevated temperature, for example in the range of from 50° C. to 120° C. and preferably in the presence of a base such as sodium hydride.

The compounds of formula (IV), (V) and (VI) are generally known commercially available compounds or are prepared using methods analogous to those used to prepare such compounds.

Suitable protecting groups in any of the abovementioned reactions are those used conventionally in the art. Thus, for example, a suitable nitrogen protecting group is a benzyl group or a benzyloxycarbonyl group a suitable hydroxyl protecting group is a benzyl group.

The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter when required the benzyl group may be conveniently removed using a mild ether cleavage reagent such as trimethylsilyliodide.

A compound of formula (I), or a tautomeric form thereof, and/or a pharmaceutically acceptable salt thereof and/or a pharmaceutically acceptable solvate thereof, may also be prepared by reacting a compound of formula (VII):

wherein $A^1$, $A^2$ X, Y and n are as defined in relation to formula (I) with 2,4-thiazolidinedione; and thereafter if required carrying out one or more of the following optional steps:

(i) converting a compound of formula (I) into a further compound of formula (I);

(ii) preparing a pharmaceutically acceptable salt of a compound of formula (I) and/or a pharmaceutically acceptable solvate thereof.

The reaction between a compound of formula (VII) and 2,4-thiazolidinedione may suitably be carried out under analogous conditions to those used in the reaction between a compound of formula (V) and 2,4-thiazolidinedione.

A compound of formula (VII) may be prepared by reacting a compound of formula (VIII):

wherein $A^2$ is as defined in relation to formula (I) and $R^a$ is as defined in relation to formula (III), with an appropriate reagent capable of converting $R^a$ to a moiety of formula (g):

wherein $A^1$, X, Y and n are as defined in relation to formula (I).

Suitable values for $R^a$ include HX—$(CH_2)_n$—Y— wherein X, Y and n are as defined in relation to the compound of formula (I). When $R^a$ represents HX—$(CH_2)_n$—Y—the appropriate compound of formula (VIII) may be reacted with a reagent of the abovedefined formula (IV) to provide the required compound of formula (VII).

Suitable reaction conditions for the reaction of the compound of formula (VIII) and the appropriate reagent may include those described above in relation to the preparation of compound (III) with the said appropriate reagent.

Suitably, in the compound of formula (VIII), $R^a$ represents a leaving group, especially a fluorine atom. When $R^a$ represents a leaving group, preferably a fluorine atom, a particularly appropriate reagent is a compound of formula (IX):

wherein $A^1$, X, Y and n are as defined in relation to formula (I).

The reaction between the compounds of formulae (VIII) and (IX) may be carried out under any suitable conditions, for example in a solvent such as dimethylformamide or dimethylsulphoxide at an elevated temperature for example in the range of between 100° to 150° C., suitably in the presence of a base such as sodium hydride or potassium carbonate.

Suitably, in the compound of formula (VIII), $R^a$ represents a hydroxyl group or a thiol group, and a particularly appropriate reagent is a compound of the abovedefined formula (IX) or a compound of formula (IXA):

wherein $A^1$, X and n are as defined in relation to formula (IX) and $R^x$ represents a tosylate or mesylate group.

The reaction between the compound of formula (VIII) wherein $R^a$ is a hydroxyl group and the reagent of the above defined formula (IX) may suitably be carried out in an aprotic solvent, such as tetrahydrofuran, at low to medium temperature, for example at ambient temperature, and preferably in the presence of a coupling agent such as that provided by triphenylphosphine and diethylazodicarboxylate.

The reaction between the compound of formula (VIII), wherein $R^a$ is a hydroxyl group or a thiol group, and the reagent of the abovedefined formula (IXA) may be carried out in an aprotic solvent, such as dimethylformamide, at a low to elevated temperature, for example in the range of from 50° C. to 120° C. and preferably in the presence of a base, such as sodium hydride.

The compound of formula (IXA) may be prepared from the corresponding compound of formula (IX) by reaction with either a tosyl halide or a mesyl halide in a solvent such as pyridine.

In one aspect of the abovementioned process for preparing a compound of formula (I), a compound of formula (I), wherein Y represents —O—, may be prepared by reacting a compound of the above defined formula (III), wherein $R^a$ is OH, with a compound of the abovedefined formula (IX) wherein Y represents —O—.

Suitable conditions for the last abovementioned reaction include analogous conditions to those disclosed above for the reaction between compounds of formulae (VA) and (VI).

In a further aspect of the above mentioned process for preparing a compound of formula (I), a compound of the above defined formula (III), wherein $R^a$ represents an —OH group or an —SH group, may be reacted with a compound of the abovedefined formula (IXA).

Suitable reaction conditions for the reaction between compounds (III) and (IXA) are analogous to those disclosed above for the reaction between the compounds of formulae (VIII) and (IXA).

The compounds of formula (VIII) are known compounds or they are compounds prepared by methods analogous to those used to prepare known compounds, for example 4-fluorobenzaldehyde and 4-hydroxybenzaldehyde are known commercially available compounds and 4-mercaptobenzaldehyde may be prepared as outlined in Beilstein 8.I.533.

The reagent of formula (IX) may be prepared by reacting a compound of the hereinabove defined formula (IV), with a compound of the hereinbefore defined formula (VI) and thereafter if required removing any nitrogen protecting group using the appropriate conventional conditions.

The reaction between the compounds of formula (IV) and (VI) may be carried out under any suitable conditions, such as in solvent, for example in an aprotic solvent such as tetrahydrofuran or dimethylformamide, at a low to medium temperature, for example a temperature in the range of from 0° to 60° C.

Favourably when $R^1$ represents hydrogen the reaction is carried out using the compound of formula (VI) as a solvent at a low to elevated temperature, suitably an elevated temperature such as in the range of between 100° and 170° C.

The abovementioned conversion of a compound of formula (I) into a further compound of formula (I) includes the following conversions:

(a) reducing a compound of formula (I) wherein $R^2$ and $R^3$ together represent a bond, to a compound of formula (I) wherein $R^2$ and $R^3$ each represent hydrogen; and (b) converting one group $R^1$ into another group $R^1$.

The conversion of a compound of formula (I) to a further compound of formula (I) may be carried out by using any appropriate conventional procedure.

A suitable reduction method for the abovementioned conversion (a) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

The abovementioned reduction of a compound of formula (III) wherein $R^2$ and $R^3$ together represent a bond to a compound of formula (III) wherein $R^2$ and $R^3$ each represent hydrogen, may be carried out under analogous conditions to those referred to above in conversion (a) of the compound of formula (I).

In the abovementioned conversion (b), suitable conversions of one group $R^1$ into another group $R^1$ includes converting a group $R^1$ which represents hydrogen into a group $R^1$ which represents an acyl group.

The conversion of a compound of formula (I) wherein $R^1$ represents hydrogen into a compound of formula (I) wherein $R^1$ represents acyl may be carried out using any appropriate conventional acylation procedure, such as by treating an appropriately protected compound of formula (I) with an acylating agent. For example acetic anhydride may be used to prepare the compound of formula (I) wherein $R^1$ is acetyl.

It will be appreciated that in the abovementioned conversions (a) and (b) any reactive group in the compound of formula (I) would be protected, according to conventional chemical practice, where necessary.

Where appropriate the isomeric forms of the compounds of formula (I) and the pharmaceutically acceptable salts thereof may be prepared as individual isomers using conventional chemical procedures.

The compounds of formula (III) and (VII) are novel compounds and as such form a further aspect of the invention.

As mentioned above the compounds of the invention are indicated as having useful therapeutic properties: The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

PROCEDURE 1

5-[4-(2-Hydroxyethoxy)benzyl]-2,4-thiazolidinedione.

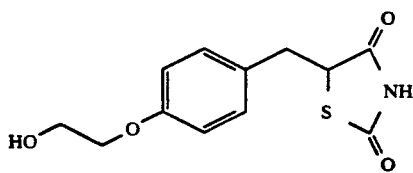

2,4-Thiazolidinedione (46g) and 4-(2-hydroxyethoxy)-benzaldehyde (65g) were mixed in toluene (400ml) containing acetic acid (1.0 ml) and piperidine (1.0 ml) in an apparatus incorporating a water-trap. The mixture was boiled under reflux with vigorous stirring for 30 minutes, during which time the theoretical quantity of water was obtained and 5-[4-(2-hydroxyethoxy)benzylidene]-2,4-thiazolidinedione started to crystallise. The solution was cooled and the benzylidene compound (mp 194° C.-196° C.) collected by filtration. This product was suspended in methanol (2 l.) and treated portionwise with magnesium turnings (2 g). When the vigorous reaction started a cooling bath was applied and the rest of the magnesium (78 g) was added portionwise with stirring. The mixture was stirred overnight at ambient temperature and the solvent was then evaporated. 5% Hydrochloric acid solution (1000 ml), water (500 ml) and methanol (500 ml) were added. When gas evolution ceased the mixture was extracted with dichloromethane, the organic phase dried (MgSO₄), filtered and evaporated under reduced pressure. The title compound was obtained pure by crystallisation from aqueous methanol (m.p. 137°-9° C.).

¹H NMR δ (DMSO-d₆)

2.9-4.2 (2H, complex); 3.7 (2H,t); 3.9 (2H,t); 4.8(1H,complex); 4.3-5.2 (1H, broad s, exchanges with D₂O); 6.85 (2H,d); 7.15 (2H,d); 11.5-12.5 (1H, broad s, exchanges with D₂O).

PROCEDURE 2

3-[(2-Benzoxazolyl)oxy]propan-1-ol

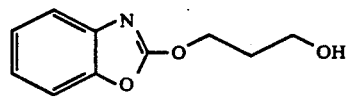

To a stirred solution of 1,3-propanediol (65 g) in dimethylformamide (60 ml) was added sodium hydride (3.0 g, 60% dispersion in oil) portionwise. The mixture was stirred until effervescence had ceased. A solution of 2-chlorobenzoxazole (11.4 g) in dimethylformamide (30 ml) was added dropwise. The reaction mixture was stirred at room temperature overnight. The mixture was added to water (600 ml) and extracted with ethyl acetate (3×300 ml). The combined organic extracts were washed with water (2×300 ml), brine (2×300 ml), dried (MgSO₄), filtered and evaporated to dryness. The title compound was obtained as an oil following chromatography on silica gel in 3% methanol in dichloromethane.

¹H NMR δ (CDCl₃)

2.15 (2H, multiplet); 3.2 (1H, t, exchanges with D₂O); 3.8 (2H, multiplet; triplet on D₂O exchange); 4.8 (2H, t); 7.2-7.7 (4H, complex).

PROCEDURE 3

3-[(2-Benzoxazolyl)oxy]propan-1-ol methanesulphonyl ester

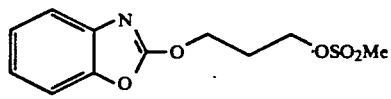

4-Methanesulphonyl chloride (3.47 g) was added dropwise to an ice cooled solution of 3-[(2-benzoxazolyl)oxy]propan-1-ol (3.9 g) in dry pyridine (30 ml). The mixture was stirred at room temperature for 16 hours, added to water (200 ml) and extracted with ethyl acetate (3×100 ml). The combined organic extracts were washed with water (2×100 ml), brine (100 ml), dried (MgSO₄), filtered and evaporated to dryness to afford the title compound which was used in the next stage without further purification.

¹H NMR δ (CDCl₃)

2.35 (2H, multiplet); 3.1 (3H, s); 4.45 (2H, t); 4.75 (2H, t); 7.2-7.65 (4H, complex).

PROCEDURE 4

4-(3-[(2-Benzoxazolyl)oxy]propoxy)benzaldehyde

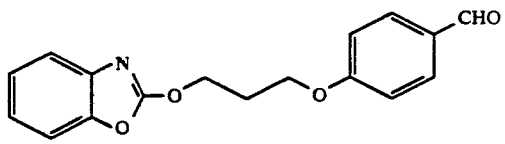

To a solution of 4-hydroxybenzaldehyde (2.33 g) in dry dimethylformamide (50 ml) was added portionwise sodium hydride (0.81 g; 60% dispersion in oil) with stirring at room temperature under an atmosphere of nitrogen. After gas evolution had ceased, a solution of 3-[(2-benzoxazolyl)oxy]propan-1-ol methanesulphonyl ester (4.7 g) in dry dimethylformamide was added dropwise. The mixture was heated to 80° C. overnight. After cooling, the mixture was added to water (500 ml) and extracted with diethyl ether (3×200 ml). The combined organic extracts were washed with sodium hydroxide solution (2.5 M; 2×200 ml), brine (2×200 ml), dried (MgSO₄), filtered and evaporated to dryness. Chromatography of the residual oil in 1% methanol in dichloromethane afforded the title compound which was used in the next stage without further purification.

$^1$H NMR δ (CDCl₃)

2.4 (2H, multiplet); 4.25 (2H, t); 4.8 (2H, t); 7.0–7.6 (6H, complex); 7.85 (2H, d); 10.0 (1H, s).

PROCEDURE 5

4-[2-(N-Methyl-N-(2-benzoxazolyl)amino)ethylthio]-benzaldehyde

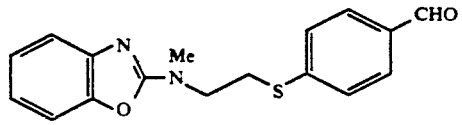

Sodium sulphide nonahydrate (6.4 g) and 4-fluorobenzaldehyde (3.3 g) in dimethylformamide (130 ml) were stirred at 80° C. under an atmosphere of nitrogen. After 4 hours, 2-(N-(2-benzoxazolyl)-N-methylamino)ethanol methanesulphonyl ester (7.2 g) in dimethylformamide (100 ml) was added dropwise over 10 minutes, and the solution stirred at 80° C. for a further 16 hours. The solution was cooled, added to water (1 l.) and extracted with diethyl ether (4×300 ml). The organic extracts were washed with brine (2×300 ml), dried (MgSO₄), filtered and evaporated to dryness. The residual oil was chromatographed on silica gel in 1% methanol in dichloromethane to afford the title compound which was used in the next stage without further purification.

$^1$H NMR δ (CDCl₃)

3.2 (3H, s); 3.35 (2H, t); 3.8 (2H, t); 6.9–7.6 (6H, complex); 7.8 (2H, d); 10.0 (1H, s).

EXAMPLE 1

5-[4-((2-(2-Benzoxazolyl)oxy)ethoxy)benzyl]-2,4-thiazolidinedione 5-(4-(2-Hydroxyethoxy)benzyl)-2,4-thiazolidinedione (3.05 g) was dissolved in dry dimethylformamide (150 ml) and sodium hydride (0.9 g, 60% dispersion in oil) was added portionwise. The mixture was stirred under nitrogen at room temperature until the reaction ceased. A solution of 2-chlorobenzoxazole (1.75 g) in dry dimethylformamide (10 ml) was added and the reaction mixture was heated overnight at 80° C. The mixture was added to iced-water, neutralised carefully with 10% hydrochloric acid and extracted with dichloromethane (2×250 ml). The combined organic extracts were washed with brine (3×250 ml), dried (MgSO₄) and evaporated to dryness. The product was chromatographed on silica-gel in dichloromethane and the title compound (mp 164°–520 C.) was obtained following crystallisation from methanol.

$^1$H NMR δ (DMSO-d₆)

3.0–3.4 (2H, complex); 4.4 (2H, complex); 4.85 (3H, complex); 6.9 (2H, d); 7.1–7.6 (6H, complex); 12.0 (1H, broad s, exchanges with D₂O).

EXAMPLE 2

5-[4-((2-(2-Pyridyl)oxy)ethoxy)benzyl]-2,4-thiazolidinedione

The title compound (mp 135° C.; MeOH) was prepared from 2-bromopyridine and 5-[4-(2-hydroxyethoxy)benzyl]-2,4-thiazolidinedione by an analogous procedure to that described in Example 1.

$^1$H NMR δ (DMSO-d₆)

3.0–3.4 (2H, complex); 4.3 (2H, t); 4.55 (2H, t); 4.85 (1H, complex); 6.6–7.0 (4H, complex); 7.2 (2H, d); 7.7 (1H, multiplet); 8.2 (1H, multiplet); 12.0 (1H, broad s exchanges with D₂O).

EXAMPLE 3

5-[4-((2-(2-Pyrimidinyl)oxy)ethoxy)benzyl]-2,4-thiazolidinedione

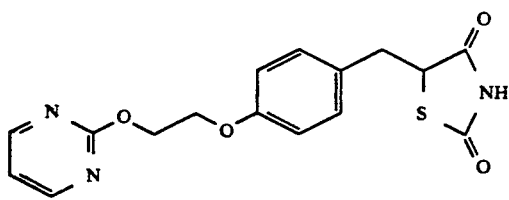

The title compound (mp 163°-4° C.; MeOH) was prepared from 2-chloropyrimidine and 5-[4-(2-hydroxyethoxy)benzyl]-2,4-thiazolidinedione by an analogous procedure to that described in Example 1.

¹H NMR δ (DMSO-d₆)

3.0-3.4 (2H, complex); 4.3 (2H, t); 4.6 (2H, t); 4.85 (1H, complex); 6.9 (2H, d); 7.15 (3H, complex); 8.6 (2H, d); 12.0 (1H, broad s exchanges with D₂O).

EXAMPLE 4

5-[4-((3-(2-Benzoxazolyl)oxy)propoxy)benzyl]-2,4-thiazolidinedione

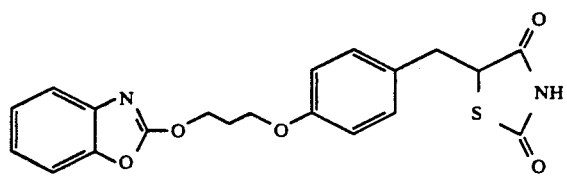

5-[4-((3-(2-Benzoxazolyl)oxy)propoxy)benzylidene]-2,4-thiazolidinedione (3 g) in dry 1,4-dioxan (100 ml) was reduced under hydrogen in the presence of 10% palladium on charcoal (6 g) at ambient temperature and atmospheric pressure until hydrogen uptake ceased. The solution was filtered through diatomaceous earth, the filter pad was washed extensively with 1,4-dioxan and the combined filtrates evaporated to dryness under vacuum. The title compound (mp 159°-60° C.) was obtained after crystallisation from methanol.

¹H NMR δ (DMSO-d₆)

2.3 (2H, multiplet); 3.0-3.4 (2H, complex); 4.15 (2H, t); 4.7 (2H, t); 4.85 (1H, complex); 6.9 (2H, d); 7.1-7.55 (6H, complex); 12.0 (1H, broad s exchanges with D₂O).

EXAMPLE 5

5-[4-((3-(2-Benzoxazolyl)oxy)propoxy)benzylidene]-2,4-thiazolidinedione

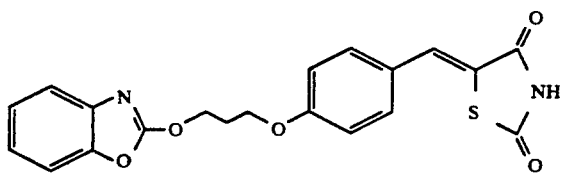

A solution of 4-[(3-(2-benzoxazolyl)oxy)propoxy]-benzaldehyde (4 g) and 2,4-thiazolidinedione (2.3 g) in toluene (150 ml) containing a catalytic quantity of piperdinium acetate was boiled under reflux in a Dean and Stark apparatus for 2 hours. The mixture was cooled and filtered to give the title compound, which was used in the next stage without further purification.

¹H NMR δ (DMSO-d₆)

2.3 (2H, multiplet); 4.15 (2H, t); 4.7 (2H, t); 7.0-7.65 (8H, complex); 7.75 (1H, s); 12.0 (1H, broad s exchanges with D₂O).

EXAMPLE 6

5-(4-[2-(N-Methyl-N-(2-benzoxazolyl)amino)ethylthio]-benzyl)-2,4-thiazolidinedione

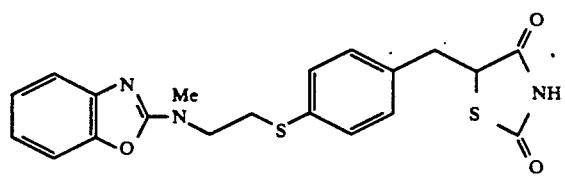

5-(4-[2-(N-Methyl-N-(2-benzoxazolyl)amino)ethylthio]-benzylidene)-2,4-thiazolidinedione (2 g) was dissolved in a mixture of methanol (70 ml) and 1,4-dioxan (70 ml). Magnesium turnings (1.7 g) were added and the solution stirred until no more effervescence was observed. The mixture was added to water (300 ml), acidified (2M HCl) to form a solution, neutralised (saturated NaHCO₃ solution) and extracted with dichloromethane (3×150 ml). The organic extracts were washed with brine 100 ml), dried (MgSO₄) and the solvent evaporated. (2×100 ml), dried (MgSO₄) and the solvent evaporated. The title compound (mp 158° C.; MeOH) was obtained following chromatography on silica gel in 1% methanol in dichloromethane.

¹H NMR δ (DMSO-d₆)

3.0-3.4 (2H, complex); 3.15 (3H, s); 3.3 (2H, t); 3.7 (2H, t); 4.9 (1H, complex); 6.95-7.45 (8H, complex); 12.0 (1H, broad s exchanges with D₂O).

EXAMPLE 7

5-(4-[2-(N-Methyl-N-(2-benzoxazolyl)amino)ethylthio]-benzylidene)-2,4-thiazolidinedione

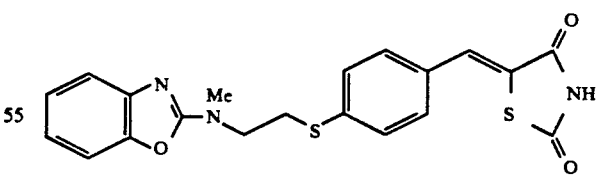

The title compound (mp 189° C.) was obtained from 4-[2-(N-methyl-N-(2-benzoxazolyl)amino)ethylthio]-benzaldehyde and 2,4-thiazolidinedione by an analogous procedure to that used in Example 5.

¹H NMR δ (DMSO-d₆)

3.15 (3H, s); 3.35 (2H, t); 3.75 (2H, t); 6.9-7.6 (8H, complex); 7.75 (1H, s); 12.0 (1H, broad s exchanges with D₂O).

DEMONSTRATION OF EFFICACY OF COMPOUND

Obese Mice, Oral Glucose Tolerance Test.

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO. | LEVEL IN DIET ($\mu$mol kg$^{-1}$ of DIET) | REDUCTION IN AREA UNDER BLOOD GLUCOSE CURVE |
|---|---|---|
| 1 | 300 | 50 |
| 2 | 300 | 20 |
| 3 | 300 | 12 |
| 4 | 300 | 32 |
| 6 | 100 | 27 |

Toxicology

No toxicological effects were indicated for any of the compounds of the invention in any of the abovementioned tests.

We claim:

1. A compound of formula (I):

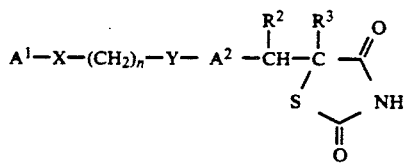

or a tautomeric form thereof and/or a pharmaceutically acceptable salt thereof and/or a pharmaceutically acceptable solvate thereof, wherein:

$A^1$ represents a substituted or unsubstituted, single or fused ring aromatic heterocyclyl group comprising 5 or 6 ring atoms in each ring and comprising 1 or 2 heteroatoms selected from oxygen, sulphur or nitrogen, optional substituents for the heterocyclyl group being up to 4 substituents selected from the group consisting of: $C_{1-12}$-alkyl, $C_{1-12}$-alkoxy, phenyl or naphthyl and halogen or any two substituents on adjacent carbon atoms, together with the carbon atoms to which they are attached, form a phenylene group, and wherein the carbon atoms of the phenylene group may themselves be substituted or unsubstituted;

$A^2$ represents a benzene ring having up to three optional substituents selected from halogen, substituted or unsubstituted $C_{1-12}$-alkoxy;

X represents O, S or $NR^1$ wherein $R^1$ represents a hydrogen atom, a $C_{1-12}$-alkyl group, a $C_{1-12}$ alkyl phenyl or $C_{1-12}$-alkyl naphthyl group, wherein the phenyl or naphthyl group may be substituted or unsubstituted, or a substituted or unsubstituted phenyl or naphthyl group;

Y represents O or S providing that Y does not represent O when represents $NR^1$;

$R^2$ and $R^3$ each represent hydrogen, or $R^2$ and $R^3$ together represent a bond;

n represents an integer in the range of from 2 to 6; and substituents for any alkyl or phenyl, naphthyl or phenylene group being up to five groups selected from halogen, $C_{1-12}$-alkyl phenyl, $C_{1-2}$-alkoxy, halo-$C_{1-12}$-alkyl, hydroxy, amino, nitro, carboxy, $C_{1-12}$-alkoxycarbonyl, $C_{1-12}$-alkoxycarbonyl-$C_{1-12}$-alkyl, $C_{1-12}$-alkylcarbonyloxy or a $C_{1-12}$-alkylcarbonyl groups.

2. A compound according to claim 1 wherein $A^1$ represents thiazolyl, oxazolyl, pyridyl or pyrimidinyl.

3. A compound according to claim 1, wherein $A^1$ represents a moiety of formula (a), (b) or (c):

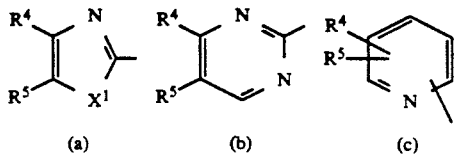

wherein:

$R^4$ and $R^5$ each independently represents a hydrogen atom, a $C_{1-12}$alkyl group or a substituted or unsubstituted phenyl or naphthyl group or when $R^4$ and $R^5$ are each attached to a carbon atom, then $R^4$ and $R^5$ together with the carbon atoms to which they are attached form a benzene ring wherein each carbon atom represented by $R^4$ and $R^5$ together may be substituted or unsubstituted; and in the moiety of formula (a)
X represents oxygen or sulphur.

4. A compound according to claim 3, wherein $R^4$ and $R^5$ each independently represent hydrogen, $C_{1-12}$ alkyl or a substituted or unsubstituted phenyl group.

5. A compound according to claim 3, wherein $R^4$ and $R^5$ together represent a moiety of formula (d):

wherein $R^6$ and $R^7$ each independently represent hydrogen, halogen, $C_{1-12}$ substituted or unsubstituted alkyl or alkoxy.

6. A compound according to claim 5, wherein $R^6$ and $R^7$ both represent hydrogen.

7. A compound according to claim 1, wherein $A^2$ represents a moiety of formula (e):

wherein $R^8$ and $R^9$ each independently represent hydrogen, halogen, $C_{1-12}$ substituted or unsubstituted alkyl or alkoxy.

8. A compound according to claim 7, wherein $R^8$ and $R^9$ each represent hydrogen.

9. A compound according to claim 1, of formula (II):

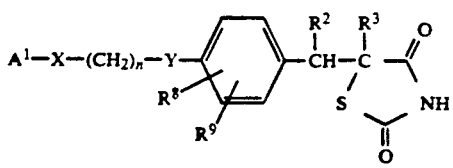

or a tautomeric form thereof and/or a pharmaceutically acceptable salt thereof and/or a pharmaceutically acceptable solvate thereof, wherein $A^1$, X, Y, $R^2$, $R^3$ and n are as defined in relation to formula (I) in claim 1 and $R^8$ and $R^9$ are as defined in relation to formula (e) in claim 7.

10. A compound according to claim 1, wherein n represents an integer 2 or 3.

11. A compound according to claim 1, wherein X and Y both represent O.

12. A compound according to claim 1, selected from the group consisting of:
   5-[4-((2-(2-benzoxazolyl)oxy)ethoxy)benzyl]-2,4-thiazolidinedione;
   5-[4-((2-(2-pyridyl)oxy)ethoxy)benzyl]-2,4-tiazolidinedione;
   5-[4-((2-(2-pyrimidinyl)oxy)ethoxy)benzyl]-2,4-thiazolidinedione;
   5-[4-((3-(2-benzoxazolyl)oxy)propoxy)benzyl]-2,4-thiazolidinedione;
   5-[4-((3-(2-benzoxazolyl)oxy)propoxy)benzylidene]-2,4-thiazolidinedione;
   5-(4-[2-(N-methyl-N-(2-benzoxazolyl)amino)ethylthio]-benzyl)-2,4-thiazolidinedione; and
   5-(4-[2-(N-methyl-N-(2-benzoxazolyl)amino)ethylthio]benzylidene)-2,4-thiazolidinedione; or a tautomeric form thereof and/or a pharmaceutically acceptable salt thereof and/or a pharmaceutically acceptable solvate thereof.

13. A pharmaceutical composition comprising a pharmaceutically effective amount of a compound of formula (I) according to claim 1, or a tautomeric form thereof or a pharmaceutically acceptable salt thereof or pharmaceutically acceptable solvate thereof, and a pharmaceutically acceptable carrier therefor.

14. A method for the treatment and/or prophylaxis of hyperglycaemia in a human or non-human mammal which comprises administering an effective, non-toxic of a compound of formula (I) according to claim 1, or a tautomeric form thereof and/or a pharmaceutically acceptable salt thereof and/or a pharmaceutically acceptable solvate thereof, to a hyperglycaemic human or non-human mammal in need thereof.

15. A method for the treatment of hyperlipidaemia in a human or non-human mammal, which comprises administering an effective, non-toxic, amount of a compound of formula (I) according to claim 1, or a tautomeric form thereof and/or a pharmaceutically acceptable salt thereof and/or a pharmaceutically acceptable solvate thereof, to a hyperlipidaemic human or non-human mammal in need thereof.

* * * * *

UNITED STATES PATENT AND TRADEMARK OFFICE
CERTIFICATE OF CORRECTION

PATENT NO. : 5,075,300

DATED : December 24, 1991

INVENTOR(S) : Richard M. Hindly, et al

It is certified that error appears in the above-identified patent and that said Letters Patent is hereby corrected as shown below:

Claim 1, column 18, line 2, after "when" insert --X--; and line 8, change "$C_{1-2}$ alkoxy" to --$C_{1-12}$ alkoxy--.

Signed and Sealed this

Thirteenth Day of April, 1993

Attest:

STEPHEN G. KUNIN

Attesting Officer     Acting Commissioner of Patents and Trademarks